(12) United States Patent
Cummings et al.

(10) Patent No.: US 7,705,017 B2
(45) Date of Patent: Apr. 27, 2010

(54) COMPOUNDS FOR TREATMENT OF NEURODEGENERATIVE DISEASES

(75) Inventors: Christopher J. Cummings, Brookline, MA (US); David A. Lowe, Park Ridge, NJ (US); William C. Ripka, San Diego, CA (US)

(73) Assignee: En Vivo Pharmaceuticals, Inc., Watertown, MA (US)

( * ) Notice: Subject to any disclaimer, the term of this patent is extended or adjusted under 35 U.S.C. 154(b) by 458 days.

(21) Appl. No.: 11/120,502

(22) Filed: May 3, 2005

(65) Prior Publication Data

US 2006/0004041 A1    Jan. 5, 2006

Related U.S. Application Data

(60) Provisional application No. 60/567,673, filed on May 3, 2004.

(51) Int. Cl.
*A61K 31/47* (2006.01)
*C07D 213/02* (2006.01)

(52) U.S. Cl. .................. 514/307; 514/309; 546/141; 546/146

(58) Field of Classification Search ........... 546/146; 514/309
See application file for complete search history.

(56) References Cited

U.S. PATENT DOCUMENTS 6,573,277 B2 * 6/2003 Thorwart et al. ............ 514/307

FOREIGN PATENT DOCUMENTS

EP    0 606 046 A1    7/1994

OTHER PUBLICATIONS

International Search Report for PCT/US05/15210 dated Jul. 14, 2005.

* cited by examiner

*Primary Examiner*—Zinna N Davis
(74) *Attorney, Agent, or Firm*—Elizabeth Spar; Kathleen Williams; Edwards Angell Palmer & Dodge LLP

(57) ABSTRACT

The present invention relates to a class of small molecule hydroxamic acid compounds capable of inhibiting histone deacetylases (HDACs). The present invention also relates to methods of preparation of hydroxamic acid HDAC inhibitor compounds of the invention, which are N-substituted-1,2,3,4-tetrahydroisoquinoline hydroxamic acid derivatives, and their incorporation into pharmaceutical compositions and methods of administration. The present invention also relates to N-substituted-1,2,3,4-tetrahydroisoquinoline hydroxamic acid derivatives, which may be prepared as a hydroxamic acid HDAC inhibitor compound library that can be utilized in screening methods known in the art.

32 Claims, No Drawings

COMPOUNDS FOR TREATMENT OF NEURODEGENERATIVE DISEASES

RELATED APPLICATIONS

This application claims priority to U.S. Provisional Application Ser. No. 60/567,673, filed on May 3, 2004, the contents of which are incorporated herein by reference.

BACKGROUND OF THE INVENTION

Histone deacetylases (HDACs) are important zinc hydrolases that are responsible for the regulation of gene expression through deacetylation of the N-acetyl lysine residues of histone proteins and other transcriptional regulators. HDACs are involved in cell-cycle progression and differentiation. HDAC inhibitors, such as trichostatin A (TSA) and suberoylanilide hydroxamic acid (SAHA), have anti-tumor effects and can inhibit cell growth, induce terminal termination, and prevent the formation of tumors in mice models.

Evidence from recent studies suggest that transcriptional dysregulation may contribute to the molecular pathogenesis of Huntington's disease (HD). HD is an inherited, progressive neurological disorder that is caused by a CAG/polyglutamine repeat expansion for which there is currently no effective therapy. It has been recently reported that administration of the potent histone deacetylase inhibitor SAHA is effective against Huntington's disease in a mouse model. Orally administered SAHA dramatically improved the motor impairment in mice. HDAC inhibitors, therefore, have the potential to be effective HD therapeutics.

The X-ray structure of an HDAC-like ortholog from the thermophilic bacterium *Aquifex aeolicus* (Histone Deacetylase-Like Protein (HDLP)—sequence family 3.40.800.20.1-1C3P.pdb) is known. For example, structures of a HDAC homologue bound to the TSA and SAHA inhibitors, have been disclosed by Finnin et al., *Science*, 401, 188, (1999).

This HDAC-like protein shares a 35% identity with human HDAC1 over 375 residues, deacetylates histones in vitro, and is inhibited by TSA and SAHA. The structure shows an active site containing a zinc-binding site and the residues making up the active site and contact the inhibitors are conserved across the known members of the HDAC family. The HDLP structure, therefore, provides a structural rationale for the design of HDAC inhibitors.

The currently known HDAC inhibitors in the art such as TSA and SAHA may pose limitations with respect to their utility. For example, the polyene chain present in TSA is potentially subject to metabolism. Also, TSA is highly hydrophobic and may be substantially protein bound. The corresponding saturated chain in SAHA is expected to reduce affinity because of entropy considerations in confining the flexible chain to a single conformation when bound in the HDAC site.

SUMMARY OF THE INVENTION

The present invention concerns a new class of HDAC inhibitors having the potential to function as therapeutics for neurodegenerative diseases. In particular, the present invention concerns hydroxamic acid compounds that are antagonists of histone deacetylases (HDACs). In one aspect, the hydroxamic acid compounds of the present invention are designed based on optional structure-interaction modeling methods and screened in silico using the histone deacetylase-like protein (HDLP) x-ray structures. The compounds of the present invention, based on their HDAC inhibition properties are, therefore, capable of providing therapeutic benefit when administered to treat HDAC mediated symptoms such as those found in neurodegenerative diseases including, for example, polyglutamine repeat disorders such as Huntington's disease, Spinocerebellar ataxias (e.g., types 1, 2, 3, 6, 7 and 17), Machado-Joseph disease, Spinal and Bulbar muscular atrophy (SBMA or Kennedy's disease), Dentatorubral Pallidoluysian Atrophy (DRPLA) and other neurological conditions arising from polyglutamine expansions, or disease arising from non-coding DNA repeat expansions such as Fragile X syndrome, Fragile XE mental retardation, Friedreich ataxia, myotonic dystrophy, Spinocerebellar ataxias (types 8, 10 and 12) or other neurodegenerative diseases such as spinal muscular atrophy (Werdnig-Hoffman disease, Kugelberg-Welander disease), Alzheimer's disease, amyotrophic lateral sclerosis, Parkinson's disease, Pick's disease, and spongiform encephalopathies.

Additional neurodegenerative diseases for which HDAC inhibitors can provide therapeutic benefit include, for example, age-related memory impairment, agyrophilic grain dementia, Parkinsonism-dementia complex of Guam, autoimmune conditions (eg Guillain-Barre syndrome, Lupus), Biswanger's disease, brain and spinal tumors (including neurofibromatosis), cerebral amyloid angiopathies (Journal of Alzheimer's Disease vol 3, 65-73 (2001)), cerebral palsy, chronic fatigue syndrome, corticobasal degeneration, conditions due to developmental dysfunction of the CNS parenchyma, conditions due to developmental dysfunction of the cerebrovasculature, dementia—multi infarct, dementia—subcortical, dementia with Lewy bodies, dementia of human immunodeficiency virus (HIV), dementia lacking distinct histology, Dementia Pugilistica, diffues neurofibrillary tangles with calcification, diseases of the eye, ear and vestibular systems involving neurodegeneration (including macular degeneration and glaucoma), Down's syndrome, dyskinesias (Paroxysmal), dystonias, essential tremor, Fahr's syndrome, fronto-temporal dementia and Parkinsonism linked to chromosome 17 (FTDP-17), frontotemporal lobar degeneration, frontal lobe dementia, hepatic encephalopathy, hereditary spastic paraplegia, hydrocephalus, pseudotumor cerebri and other conditions involving CSF dysfunction, Gaucher's disease, Hallervorden-Spatz disease, Korsakoff's syndrome, mild cognitive impairment, monomelic amyotrophy, motor neuron diseases, multiple system atrophy, multiple sclerosis and other demyelinating conditions (eg leukodystrophies), myalgic encephalomyelitis, myoclonus, neurodegeneration induced by chemicals, drugs and toxins, neurological manifestations of AIDS including AIDS dementia, neurological/cognitive manifestations and consequences of bacterial and/or virus infections, including but not restricted to enteroviruses, Niemann-Pick disease, non-Guamanian motor neuron disease with neurofibrillary tangles, non-ketotic hyperglycinemia, olivo-ponto cerebellar atrophy, oculopharyngeal muscular dystrophy, neurological manifestations of Polio myelitis including non-paralytic polio and post-polio-syndrome, primary lateral sclerosis, prion diseases including Creutzfeldt-Jakob disease (including variant form), kuru, fatal familial insomnia, Gerstmann-Straussler-Scheinker disease and other transmissible spongiform encephalopathies, prion protein cerebral amyloid angiopathy, postencephalitic Parkinsonism, progressive muscular atrophy, progressive bulbar palsy, progressive subcortical gliosis, progressive supranuclear palsy, restless leg syndrome, Rett syndrome, Sandhoff disease, spasticity, sporadic fronto-temporal dementias, striatonigral degeneration, subacute sclerosing panencephalitis, sulphite oxidase deficiency, Sydenham's chorea, tangle only dementia, Tay-Sach's disease, Tourette's syndrome, vascular dementia, and Wilson disease.

Further, HDAC inhibitors as disclosed herein can potentially provide therapeutic benefit for additional neurological disorders in which histone deacetylase and/or transcriptional repression is implicated or involved in the pathology. Examples include schizophrenia, depressive disorders, bipolar disorder, and epilepsy.

Based on their structural biological activity properties, hydroxamic acid compounds, and methods of treating diseases either associated with or mediated by HDAC function are disclosed. Moreover, the compounds of the present invention avoid the potential limitations of compounds with TSA and SAHA-like structures in providing an effective therapy for such symptoms.

In another aspect, the present invention provides small-molecule compounds that can function as HDAC inhibitors. The compounds of the invention may be preferably used to inhibit deacetylation of the N-acetyl lysine residues of histone proteins and other transcriptional regulators. The HDAC inhibitor compounds of the present invention are N-substituted-1,2,3,4-tetrahydroisoquinoline hydroxamic acid compounds.

The hydroxamic acid HDAC inhibitor compounds of the present invention are represented by structural Formula (I).

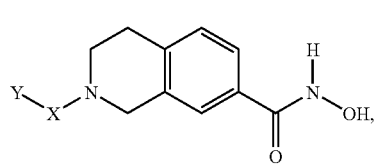
(I)

wherein:

X is selected from the group consisting of a carbonyl group (C=O), or a sulfonyl group (SO$_2$);

Y is selected from the group consisting of C$_1$-C$_6$ alkyl, R$_1$(R$_2$)N—(CH$_2$)$_n$—,

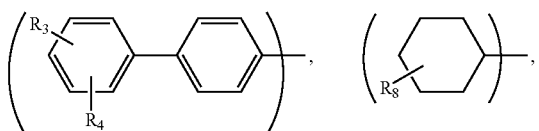

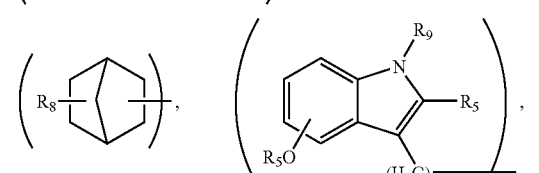

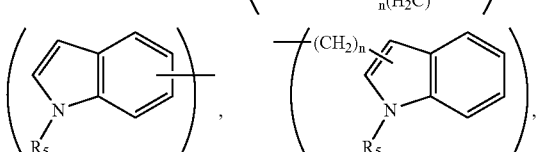

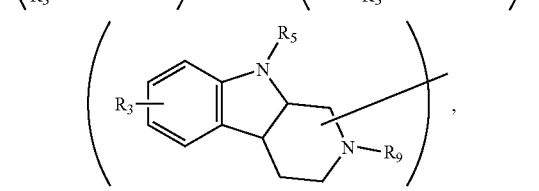

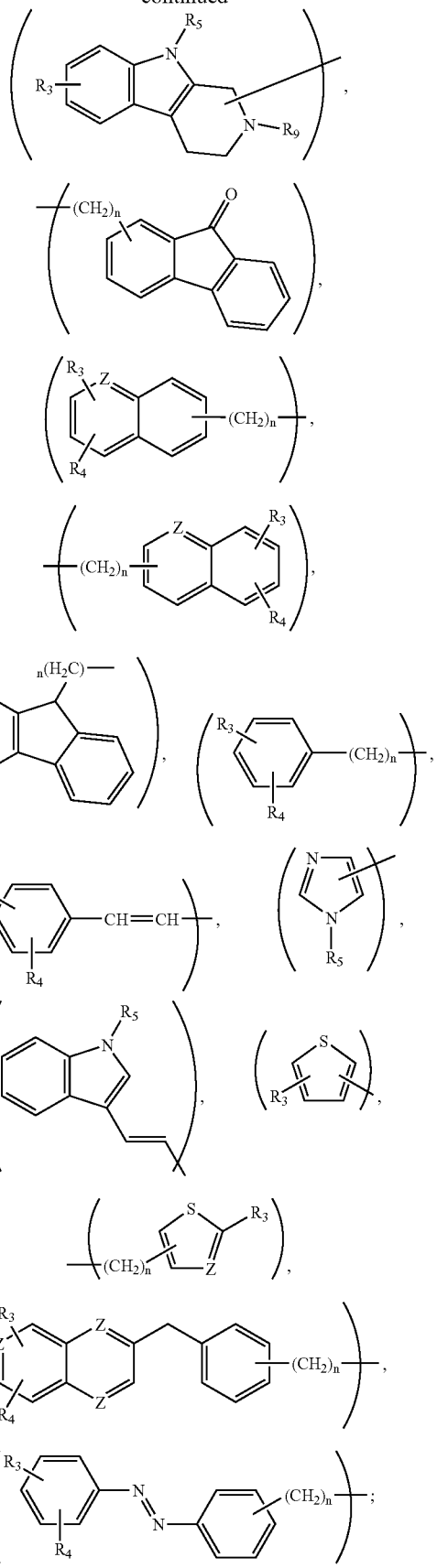

wherein:

R₁ and R₂ are each independently selected from the group consisting of hydrogen, straight chain lower alkyl, and branched lower alkyl;

R₁ and R₂, taken together with the nitrogen to which they are attached, form a heterocyclic ring, wherein said heterocyclic ring is optionally substituted with a substituted or unsubstituted lower alkyl group, or a substituted or unsubstituted benzyl group;

R₃ and R₄ are each independently selected from the group consisting of hydrogen, halogen, straight chain $C_1$-$C_8$ alkyl, $(R_1)(R_2)N$—$(CH_2)_n$—, $NH_2$—$C(=NH)$—$NH$—, $OR_5$, $CF_3$, $NO_2$, $R_7$—$C(=O)N(R_6)$—, imidazolyl, and pyrrazolyl, wherein R₁ and R₂ are as defined above;

R₅ is hydrogen, $C_1$-$C_8$ alkyl, or benzyl;

R₆ is hydrogen, lower alkyl, or benzyl;

R₇ is $C_1$-$C_8$ alkyl, benzylalkyl, heteroalkyl or heteroaralkyl;

R₈ is hydrogen, —$(CH_2)_nN(R_1)(R_2)$, or $OR_5$, wherein R₁, R₂ and R₅ are as defined above;

R₉ is hydrogen, $C_1$-$C_8$ alkyl, or benzyl;

Z is —C(R₃)— or nitrogen (N), wherein R3 is as defined above; and n is 0 to 6;

or hydrates, polymorphs, or pharmaceutically acceptable salts thereof.

The hydroxamic acid compounds of the invention can be used as active ingredients in medicament a drug formulations for treatment or prevention of a disease associated with HDACs. The present invention also contemplates use of such compounds in pharmaceutical compositions for oral or parenteral administration, comprising one or more of the hydroxamic acid compounds disclosed herein.

In yet another aspect, the present invention relates to a method of treatment, including prophylactic and therapeutic treatments, of a disease or symptoms arising from or associated with HDACs. The invention further relates to methods of antagonizing HDAC proteins, by administering oral or parenteral formulations comprising the compounds of this invention by standard methods known in the medical practice.

DETAILED DESCRIPTION OF THE INVENTION

The present invention concerns small molecule HDAC inhibitor compounds. Particularly, the present invention relates to N-substituted-1,2,3,4-tetrahydroisoquinoline hydroxamic acid compounds capable of inhibiting HDACs, that may be used to inhibit deacetylation of the N-acetyl lysine residues in histone proteins and other transcriptional regulators.

As used herein, an "HDAC inhibitor" is a compound capable of inhibiting (i.e., reduce or prevent, in whole or in part) deacetylation of the N-acetyl lysine residues of histone proteins and other transcriptional regulators. More specifically, an HDAC inhibitor is a compound that is capable of inhibiting the activity of a protein that is a member of the histone deacetylase (HDAC) family. A compound is an "HDAC inhibitor" if it reduces HDAC activity assayed as described herein in Example 10 by at least 10% relative to the assay performed in the absence of that compound.

The hydroxamic acid compounds of the present invention are represented by Structural Formula (I).

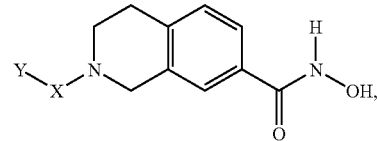

(I)

wherein:

X is selected from the group consisting of a carbonyl group (C=O), or a sulfonyl group ($SO_2$);

Y is selected from the group consisting of $C_1$-$C_6$ alkyl, $R_1(R_2)N$—$(CH_2)_n$—,

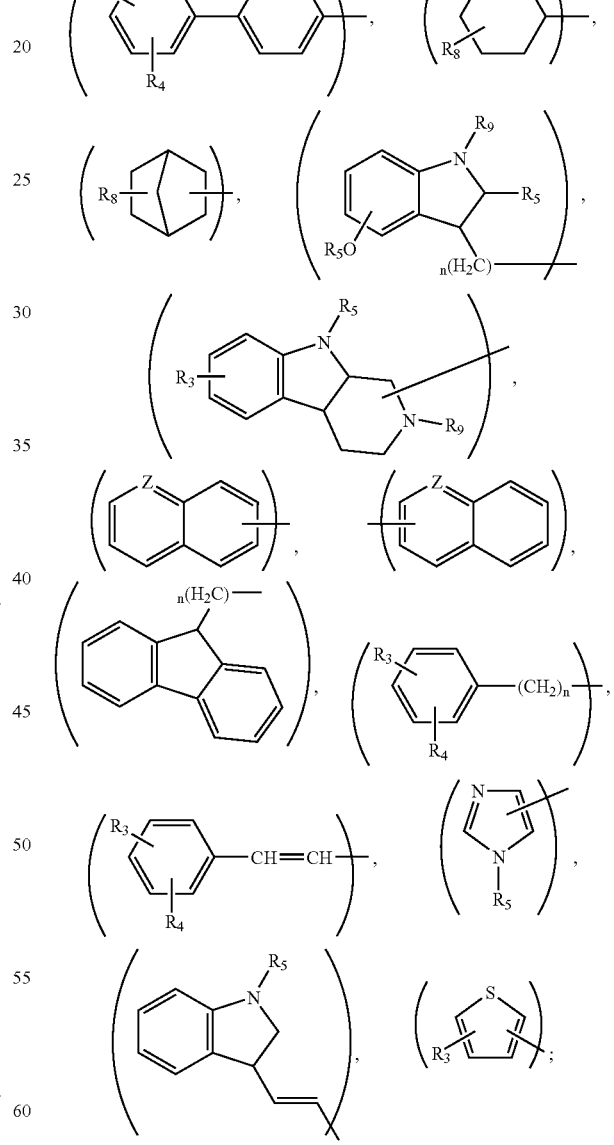

wherein:

R₁ and R₂ are each independently selected from the group consisting of hydrogen, straight chain lower alkyl, and branched lower alkyl;

$R_1$ and $R_2$, taken together with the nitrogen to which they are attached, form a heterocyclic ring, wherein said heterocyclic ring is optionally substituted with a substituted or unsubstituted lower alkyl group, or a substituted or unsubstituted benzyl group;

$R_3$ and $R_4$ are each independently selected from the group consisting of hydrogen, halogen, straight chain $C_1$-$C_8$ alkyl, $(R_1)(R_2)N$—$(CH_2)_n$—, $NH_2$—$C(=NH)$—$NH$—, $OR_5$, $CF_3$, $NO_2$, $R_7$—$C(=O)N(R_6)$—, imidazolyl, and pyrrazolyl, wherein $R_1$ and $R_2$ are as defined above;

$R_5$ is hydrogen, $C_1$-$C_8$ alkyl, or benzyl;

$R_6$ is hydrogen, lower alkyl, or benzyl;

$R_7$ is $C_1$-$C_8$ alkyl, benzylalkyl, heteroalkyl or heteroaralkyl;

$R_8$ is hydrogen, —$(CH_2)_nN(R_1)(R_2)$, or $OR_5$, wherein $R_1$, $R_2$ and $R_5$ are as defined above;

$R_9$ is hydrogen, $C_1$-$C_8$ alkyl, or benzyl;

Z is —$C(R_3)$— or nitrogen (N), wherein R3 is as defined above; and n is 0 to 6;

or hydrates, polymorphs, or pharmaceutically acceptable salts thereof.

In one embodiment, the hydroxamic acid compounds of the present invention are represented by Structural Formula (I).

wherein:

X is a carbonyl group (C=O);

Y is selected from the group consisting of $R_1$ $(R_2)N$—$(CH_2)_n$—, wherein:

$R_1$ and $R_2$ are each independently selected from the group consisting of hydrogen, straight chain lower alkyl, and branched lower alkyl;

$R_1$ and $R_2$, taken together with the nitrogen to which they are attached, form a heterocyclic ring, wherein said heterocyclic ring is optionally substituted with a substituted or unsubstituted lower alkyl group, or a substituted or unsubstituted benzyl group;

$R_3$ and $R_4$ are each independently selected from the group consisting of hydrogen, halogen, straight chain $C_1$-$C_8$ alkyl, $(R_1)(R_2)N$—$(CH_2)_n$—, $NH_2$—$C(=NH)$—$NH$—, $OR_5$, $CF_3$, $NO_2$, $R_7$—$C(=O)N(R_6)$—, imidazolyl, and pyrrazolyl, wherein $R_1$ and $R_2$ are as defined above;

$R_5$ is hydrogen, $C_1$—$C_8$ alkyl, or benzyl;

$R_6$ is hydrogen, lower alkyl, or benzyl;

$R_7$ is $C_1$-$C_8$ alkyl, benzylalkyl, heteroalkyl or heteroaralkyl;

Z is —$C(R_3)$— or nitrogen (N), wherein R3 is as defined above; and n is 0 to 6;

or hydrates, polymorphs, or pharmaceutically acceptable salts thereof.

The term "aryl group", as used herein, includes both carbocyclic and heterocyclic aromatic ring systems. An aryl group is optionally fused to a carbocyclic non-aromatic ring, a heterocyclic non-aromatic ring, a heterocyclic aromatic ring or another carbocyclic aromatic ring. A carbocyclic aromatic system consists only of carbon ring atoms, preferably up to ten.

A "halogen" as used herein, includes fluorine, chlorine, bromine and iodine atoms.

A "lower-alkyl group" as used herein, is a saturated straight chained or branched hydrocarbon. Typically, lower-alkyl groups have from one to eight carbons. Preferably, lower-alkyl groups have from one to six carbon atoms.

A "cycloalkyl group" as used herein, is a non-aromatic carbocyclic ring system that has 3 to 10 atoms. A cycloalkyl group can optionally be fused to a carbocyclic non-aromatic ring, carbocyclic aromatic ring, a heterocyclic aromatic ring, non-aromatic heterocyclic ring, or another non-aromatic carbocyclic ring. Examples of a cycloalkyl group include cyclopentyl and cyclohexyl. Examples of a cycloalkyl ring fused with an aromatic ring, include 1,2,3,4-tetrahydronaphthyl and 1,2,3-tetrahydroindanyl.

A "heteroalkyl group" as used herein, is a lower alkyl group in which at least one methylene group has been replaced with a heteroatom, such as nitrogen, oxygen, or sulfur.

A "heterocyclic group" or "heterocyclic ring" as used herein, is a ring system that has 3 to 10 atoms and includes at least one heteroatom, such as nitrogen, oxygen, or sulfur. A heterocyclic group can include a "heterocycloalkyl group" and a "heteroaryl group".

A "heterocycloalkyl group" or a "non-aromatic heterocyclic group", as used herein, is a non-aromatic ring system that has 3 to 10 atoms and includes at least one heteroatom, such as nitrogen, oxygen, or sulfur. A heterocycloalkyl group is optionally fused to a carbocyclic non-aromatic ring, carbocyclic aromatic ring, a heterocyclic aromatic ring, or another non-aromatic heterocyclic ring. Examples of heterocycloalkyl groups include piperazinyl, piperidinyl, homopiperazinyl, quinuclidinyl, azetidinyl, morpholinyl, thiomorpholinyl, thiazolidinyl, 1,2,3,4-tetrahydroquinolinyl, 1,2,3-tetrahydroindolyl, indolyl, furanyl or imidazolyl.

A "heteroaryl group" or an "aromatic heterocyclic group", as used herein, is an aryl group that has 3 to 10 ring atoms including one or more ring heteroatoms such as nitrogen, oxygen and sulfur. A heteroaryl group can be monocyclic. Alternatively, a monocyclic heteroaryl group is fused to one or more other monocyclic heteroaryl groups or monocyclic carbocyclic aryl groups. Preferably a heteroaryl group has 1 to 3 heteroatoms. A heteroaryl group is optionally fused to a carbocyclic aromatic ring, carbocyclic non-aromatic ring or another heteroaryl ring. Examples of a heteroaryl group include but are not limited to thienyl, pyridyl, pyrazolyl, isoxazolyl, thiadiazolyl, oxadiazolyl, indazolyl, furyl, pyrrolyl, imidazolyl, pyrazolyl, triazolyl, pyrimidinyl, pyridazinyl, pyrazinyl, thiazolyl, isoxazolyl, isothiazolyl, tetrazolyl, oxazolyl, oxadiazolyl, quinolinyl, carbazolyl, benzocarbazolyl, benzotriazolyl, benzimidazole, benzothiophene, benzofuran or indolyl.

An "aralkyl" group refers to an aryl-alkyl group having from about 7 to about 15 carbon atoms. Examples of aralkyl groups include, but are not limited to, benzyl, phenethyl, benzydryl, and naphthylmethyl.

A "heteroaralkyl" group refers to an aryl-alkyl group having from about 4 to about 15 carbon atoms, including one or more ring heteroatoms such as nitrogen, oxygen and sulfur.

Suitable substituents on a substituted benyzlalkyl group, substituted lower-alkyl group, substituted heteroalkyl group, substituted cycloalkyl group, substituted heterocycloalkyl group, substituted aryl group, substituted heteroaryl group, substituted aralkyl group, substituted heteroaralkyl group include for example but are not limited to, hydrogen, halogen, an electron withdrawing group, a hydroxy group, an alkoxy group, a lower alkyl group, a cycloalkyl group, a heterocycloalkyl group, an aryl group, a heteroaryl group, an aralkyl group, a heteroaralkyl group, $(R_1)(R_2)N-(CH_2)_n-$, $NH_2-C(=NH)-NH-$, $OR_5$, $CF_3$, $NO_2$, $R_7-C(=O)N(R_6)-$, and imidazolyl. $R_1$, $R_2$, $R_5$ $R_6$ and $R_7$ are as defined above;

A substituted lower-alkyl group, substituted heteroalkyl group, substituted cycloalkyl group, substituted heterocycloalkyl group, substituted aryl group, substituted heteroaryl group, substituted aralkyl group, substituted heteroaralkyl group can have more than one substituent.

Currently preferred hydroxamic acid HDAC inhibitor compounds include, but are not limited to:

2-(4-guanidino-benzoyl)-1,2,3,4-tetrahydro-isoquinoline-7-carboxylic acid hydroxyamide, 2-(4-dimethylamino-benzoyl)-1,2,3,4-tetrahydro-isoquinoline-7-carboxylic acid hydroxyamide, 2-(quinoline-8-carbonyl)-1,2,3,4-tetrahydro-isoquinoline-7-carboxylic acid hydroxyamide, 2-((4-dimethylamino-phenyl)-acetyl)-1,2,3,4-tetrahydro-isoquinoline-7-carboxylic acid hydroxyamide, 2-(4-dimethylamino-butyryl)-1,2,3,4-tetrahydro-isoquinoline-7-carboxylic acid hydroxyamide, or 2-(4-imidazol-1-yl-benzoyl)-1,2,3,4-tetrahydro-isoquinoline-7-carboxylic acid hydroxyamide.

The hydroxamic acid HDAC inhibitor compounds of the present invention can exist as water soluble salts, polymorphic crystalline forms, and in some cases as optically active stereoisomers and their racemates. All such variants including physiologically acceptable salts and isomers of such compounds are within the scope of the claims.

Salts of compounds containing an amine or other basic group can be obtained, for example, by reacting with a suitable organic or mineral acid, such as for example hydrochloric acid, perchloric acid, acetic acid, citric acid, maleic acid, and the like. Compounds with a quaternary ammonium group also contain a counter-ion such as chloride, bromide, iodide, acetate, perchlorate and the like. Salts of compounds containing a carboxylic acid or other acidic functional group can be prepared by reaction with a suitable base, for example, a alkali metal hydroxide base. Salts of acidic functional groups contain a counter-ion such as sodium, potassium, ammonium, calcium and the like.

The hydroxamic acid HDAC inhibitor compounds of the present invention can be synthesized by using a combination of any suitable method known in the art. In one embodiment, a typical synthetic process for obtaining compounds of the invention is carried out as shown in Scheme 1.

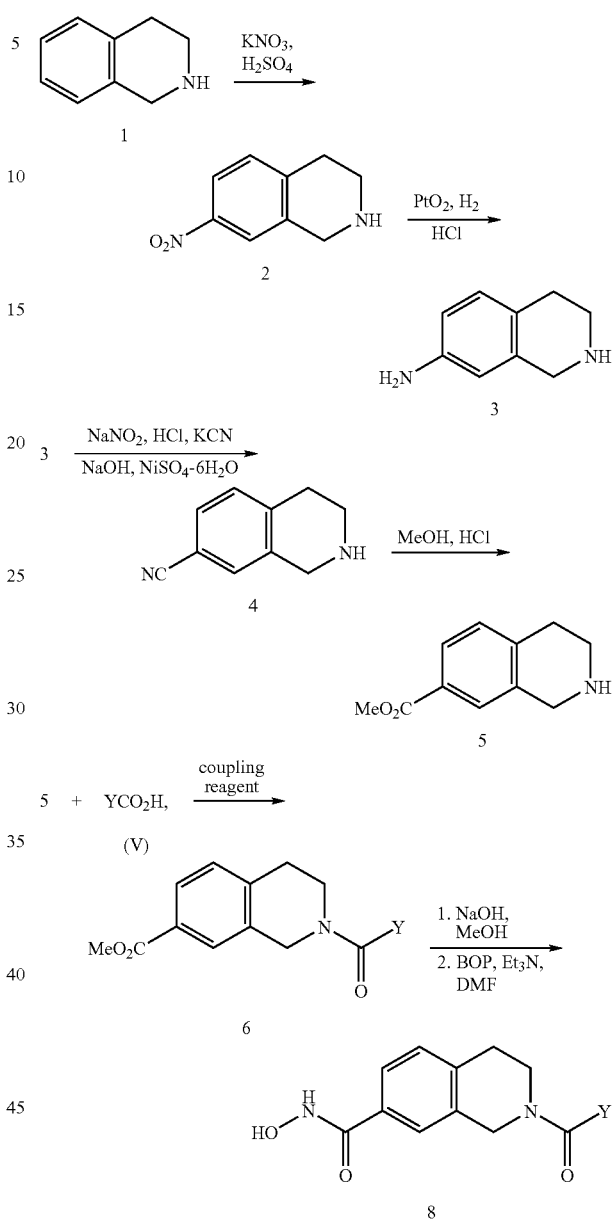

Scheme 1.

7-Amino-1,2,3,4-tetrahydroisoquinoline 3 and 6-Cyanotetrahydroquinoline 4 is obtained by subjecting readily available 1,2,3,4-tetrahydroisoquinoline 1 to a series of steps known in the art in the art (See for example, Grunewald et al., J. Med. Chem. 1997, 40, 3997-4005, the contents of which is incorporated herein by reference in its entirety). 6-Cyanotetrahydroquinoline 4 is then reacted with an aliphatic alcohol, such as for example, methanol (MeOH) and hydrochloric acid (HCl) to form 7-Methoxycarbonyltetrahydroiosquinoline 5. Methoxycarbonyltetrahydroiosquinoline 5 is then reacted with a carboxylic acid $YCO_2H$ (V) to form amide 6. Y is as described above. Examples of preferred carboxylic acids (V) include but are not limited to compounds 10-47 listed in Table 1. Amide 6 is subsequently reacted in the presence of an alcoholic base solution, (such as for example, sodium hydroxide (NaOH) in methanol (MeOH)). with 1-benzotriazolyoxytris(dimethylamino)phosphonium hexafluorophosphate (Castro's Reagent) (BOP), triethylamine (Et₃N) in N,N-dimethylformamide (DMF) to form hydroxamic acid 8, a Formula I compound.

Alternatively, methoxycarbonyltetrahydroiosquinoline 5 is reacted with a sulfonyl chloride YSO₂Cl (VIII) to form the corresponding sulfonyl compound 7 as shown in Scheme 2. Examples of preferred sulfonyl chloride compounds include but are not limited to compounds 48-67 as listed in Table 2. Sulfonyl 7 is subjected to the same sequence of reactions as amide 6 to give hydroxamic acid 9, a Formula I compound.

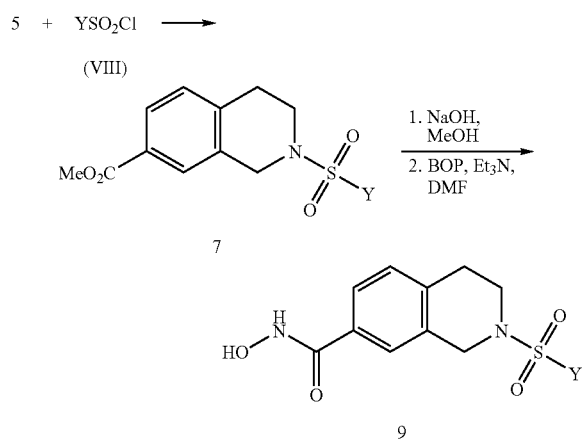

Scheme 2.

The synthetic process described above is intended to exemplify a method of obtaining a hydroxamic acid HDAC inhibitor compound of the invention to one skilled in the art, and is not intended to, in any way, limit the scope of the invention.

TABLE 1

Carboxylic Acids of Formula YCO₂H (V)

| Compound Number. | Chemical Name |
|---|---|
| 10 | 4-(dimethylamino)benzoic acid |
| 11 | 3-(dimethylamino)benzoic acid |
| 12 | 8-quinolinecarboxylic acid |
| 13 | 4-biphenylcarboxylic acid |
| 14 | 4-(dimethylamino)phenylacetic acid |
| 15 | 9-fluorenone-2-carboxylic acid |
| 16 | 4'-(octyloxy)-4-biphenylcarboxylic acid |
| 17 | 4-(dimethylamino)cinnamic acid |
| 18 | 9-fluoreneacetic acid |
| 19 | 1-naphthylacetic acid |
| 20 | 2-naphthylacetic acid |
| 21 | 1-naphthoic acid |
| 22 | 2-naphthoic acid |
| 23 | 4-(dimethylamino)butyric acid hydrochloride |
| 24 | 3-quinolinecarboxylic acid |
| 25 | 4-(1H-imidazol-1-yl)benzoic acid |
| 26 | 4-(1H-pyrrol-1-yl)benzoic acid |
| 27 | 2-hydroxy-5-(1H-pyrrol-1-yl)benzoic acid |
| 28 | 4-(N-(2,4-diamino-6-pteridinylmethyl)-N-methylamino)benzoic acid |
| 29 | 4-imidazolecarboxylic acid |
| 30 | 4-(dimethylamino)butyric acid |
| 31 | 6-methoxy-1,2,3,4-tetrahydro-9H-pyrido[3,4b]-indo carboxylic acid |
| 32 | trans-3-indoleacrylic acid |
| 33 | 4-acetamidobenzoic acid |
| 34 | 4-guanidinobenzoic acid hydrochloride |
| 35 | indole-5-carboxylic acid |

TABLE 1-continued

Carboxylic Acids of Formula YCO₂H (V)

| Compound Number. | Chemical Name |
|---|---|
| 36 | cyclohexane carboxylic acid |
| 37 | cis-4-amino-1-cyclohexane carboxylic acid |
| 38 | trans-4-(aminomethyl)cyclohexane carboxylic acid |
| 39 | 4-methoxycyclohexane carboxylic acid |
| 40 | 2-amino-3-norbornane carboxylic acid |
| 41 | 1-amino-1-cyclohexane carboxylic acid |
| 42 | 2-amino-1-cyclohexane carboxylic acid |
| 43 | 4'-hydroxy-4-biphenylcarboxylic acid |
| 44 | (S)-(−)-2,3,4,9-tetrahydro-1H-pyrido[3,4-b]indole-3-carboxylic acid |
| 45 | 5-methoxy-2-methyl-3-indole acetic acid |
| 46 | 3-indolebutyric acid |
| 47 | 1-methyl-3-indole acetic acid |

TABLE 2

Sulfonyl Chlorides of Formula YSO₂Cl (VIII)

| Compound Number | Chemical Name |
|---|---|
| 48 | benzene sulfonyl chloride |
| 49 | biphenyl-4-sulfonyl chloride |
| 50 | 1-naphthalene sulfonyl chloride |
| 51 | N-acetyl sulfanilyl chloride |
| 52 | 4-chlorobenzene sulfonyl chloride |
| 53 | 2-naphthalene sulfonyl chloride |
| 54 | trans-beta-styrenesulfonyl chloride |
| 55 | alpha-toluenesulfonyl chloride |
| 56 | 4-nitorbenzenesulfonyl chloride |
| 57 | 3,4-dimethoxybenzenesulfonyl chloride |
| 58 | 4-methoxybenzenesulfonyl chloride |
| 59 | 8-quinoline sulfonyl chloride |
| 60 | 2-thiophene sulfonyl chloride |
| 61 | 3,5-dichlorobenzenesulfonyl chloride |
| 62 | 3,4-difluorobenzenesulfonyl chloride |
| 63 | 4-(trifluoromethyl)benzenesulfonyl chloride |
| 64 | dansyl chloride |
| 65 | 4-bromobenzenesulfonyl chloride |
| 66 | 4-(dimethylamino)azobenzene-4'-sulfonyl chloride |
| 78 | 2-acetamideo-4-methyl-5-thiazolesulfonyl chloride |

TABLE 3

Hydroxamic Acid HDAC Inhibitor Compounds*

| Compound Number | Product |
|---|---|
| 68 | 2-(4-Acetylamino-benzoyl)-1,2,3,4-tetrahydro-isoquinoline-7-carboxylic acid hydroxyamide |
| 69 | 2-(4-Guanidino-benzoyl)-1,2,3,4-tetrahydro-isoquinoline-7-carboxylic acid hydroxyamide |
| 70 | 2-(1H-Indole-5-carbonyl)-1,2,3,4-tetrahydro-isoquinoline-7-carboxylic acid hydroxyamide |
| 71 | 2-(4-Cyclohexanecarbonyl-benzoyl)-1,2,3,4-tetrahydro-isoquinoline-7-carboxylic acid hydroxyamide |
| 72 | 2-(4-Amino-cyclohexanecarbonyl)-1,2,3,4-tetrahydro-isoquinoline-7-carboxylic acid hydroxyamide |
| 73 | 2-(4-Aminomethyl-cyclohexanecarbonyl)-1,2,3,4-tetrahydro-isoquinoline-7-carboxylic acid hydroxyamide |
| 74 | 2-(4-Methoxy-cyclohexanecarbonyl)-1,2,3,4-tetrahydro-isoquinoline-7-carboxylic acid hydroxyamide |
| 75 | 2-(3-Amino-bicyclo[2.2.1]heptane-2-carbonyl)-1,2,3,4-tetrahydro-isoquinoline-7-carboxylic acid hydroxyamide |
| 76 | 2-(1-Amino-cyclohexanecarbonyl)-1,2,3,4-tetrahydro-isoquinoline-7-carboxylic acid hydroxyamide |
| 77 | 2-(2-Amino-cyclohexanecarbonyl)-1,2,3,4-tetrahydro-isoquinoline-7-carboxylic acid hydroxyamide |

TABLE 3-continued

Hydroxamic Acid HDAC Inhibitor Compounds*

| Compound Number | Product |
|---|---|
| 78 | 2-(4'-Hydroxy-biphenyl-4-carbonyl)-1,2,3,4-tetrahydro-isoquinoline-7-carboxylic acid hydroxyamide |
| 79 | 2-(2,3,4,9-Tetrahydro-1H-β-carboline-3-carbonyl)-1,2,3,4-tetrahydro-isoquinoline-7-carboxylic acid hydroxyamide |
| 80 | 2-[(5-Methoxy-3-methyl-1H-indol-2-yl)-acetyl]-1,2,3,4-tetrahydro-isoquinoline-7-carboxylic acid hydroxyamide |
| 81 | 2-(4-1H-Indol-2-yl-butyryl)-1,2,3,4-tetrahydro-isoquinoline-7-carboxylic acid hydroxyamide |
| 82 | 2-[(1H-Indol-2-yl)-acetyl]-1,2,3,4-tetrahydro-isoquinoline-7-carboxylic acid hydroxyamide |
| 83 | 2-(4-Dimethylamino-benzoyl)-1,2,3,4-tetrahydro-isoquinoline-7-carboxylic acid hydroxyamide |
| 84 | 2-(3-Dimethylamino-benzoyl)-1,2,3,4-tetrahydro-isoquinoline-7-carboxylic acid hydroxyamide |
| 85 | 2-(Quinoline-8-carbonyl)-1,2,3,4-tetrahydro-isoquinoline-7-carboxylic acid hydroxyamide |
| 86 | 2-(Biphenyl-4-carbonyl)-1,2,3,4-tetrahydro-isoquinoline-7-carboxylic acid hydroxyamide |
| 87 | 2-[(4-Dimethylamino-phenyl)-acetyl]-1,2,3,4-tetrahydro-isoquinoline-7-carboxylic acid hydroxyamide |
| 88 | 2-(9-Oxo-9H-fluorene-2-carbonyl)-1,2,3,4-tetrahydro-isoquinoline-7-carboxylic acid hydroxyamide |
| 89 | 2-(4'-Octyloxy-biphenyl-4-carbonyl)-1,2,3,4-tetrahydro-isoquinoline-7-carboxylic acid hydroxyamide |
| 90 | 2-[3-(4-Dimethylamino-phenyl]-acryloyl]-1,2,3,4-tetrahydro-isoquinoline-7-carboxylic acid hydroxyamide |
| 91 | 2-[(9H-Fluoren-9-yl)-acetyl]-1,2,3,4-tetrahydro-isoquinoline-7-carboxylic acid hydroxyamide |
| 92 | 2-(Naphthalen-1-yl-acetyl)-1,2,3,4-tetrahydro-isoquinoline-7-carboxylic acid hydroxyamide |
| 93 | 2-(Naphthalen-2-yl-acetyl)-1,2,3,4-tetrahydro-isoquinoline-7-carboxylic acid hydroxyamide |
| 94 | 2-(Naphthalene-1-carbonyl)-1,2,3,4-tetrahydro-isoquinoline-7-carboxylic acid hydroxyamide |
| 95 | 2-(Naphthalene-2-carbonyl)-1,2,3,4-tetrahydro-isoquinoline-7-carboxylic acid hydroxyamide |
| 96 | 2-(4-Dimethylamino-butyryl)-1,2,3,4-tetrahydro-isoquinoline-7-carboxylic acid hydroxyamide |
| 97 | 2-(Quinoline-3-carbonyl)-1,2,3,4-tetrahydro-isoquinoline-7-carboxylic acid hydroxyamide |
| 98 | 2-(4-Imidazol-1-yl-benzoyl)-1,2,3,4-tetrahydro-isoquinoline-7-carboxylic acid hydroxyamide |
| 99 | 2-(4-Pyrrol-1-yl-benzoyl)-1,2,3,4-tetrahydro-isoquinoline-7-carboxylic acid hydroxyamide |
| 100 | 2-(2-Hydroxy-4-pyrrol-1-yl-benzoyl)-1,2,3,4-tetrahydro-isoquinoline-7-carboxylic acid hydroxyamide |
| 101 | 2-{4-[(5,7-Diamino-pyrido[3,4-b]pyrazin-3-ylmethyl)-methyl-amino]-benzoyl}-1,2,3,4-tetrahydro-isoquinoline-7-carboxylic acid hydroxyamide |
| 102 | 2-(1H-Imidazole-4-carbonyl)-1,2,3,4-tetrahydro-isoquinoline-7-carboxylic acid hydroxyamide |
| 103 | 2-(4-Dimethylamino-butyryl)-1,2,3,4-tetrahydro-isoquinoline-7-carboxylic acid hydroxyamide |
| 104 | 2-(6-Methoxy-2,3,4,4a,9,9a-hexahydro-1H-β-carboline-1-carbonyl)-1,2,3,4-tetrahydro-isoquinoline-7-carboxylic acid hydroxyamide |
| 105 | 2-(3-1H-Indol-3-yl-acryloyl)-1,2,3,4-tetrahydro-isoquinoline-7-carboxylic acid hydroxyamide |
| 106 | 2-Benzenesulfonyl-1,2,3,4-tetrahydro-isoquinoline-7-carboxylic acid hydroxyamide |
| 107 | 2-(Biphenyl-4-sulfonyl)-1,2,3,4-tetrahydro-isoquinoline-7-carboxylic acid hydroxyamide |
| 108 | 2-(Naphthalene-1-sulfonyl)-1,2,3,4-tetrahydro-isoquinoline-7-carboxylic acid hydroxyamide |
| 109 | 2-(4-Acetylamino-benzenesulfonyl)-1,2,3,4-tetrahydro-isoquinoline-7-carboxylic acid hydroxyamide |
| 110 | 2-(4-Chloro-benzenesulfonyl)-1,2,3,4-tetrahydro-isoquinoline-7-carboxylic acid hydroxyamide |
| 111 | 2-(Naphthalene-2-sulfonyl)-1,2,3,4-tetrahydro-isoquinoline-7-carboxylic acid hydroxyamide |
| 112 | 2-(2-Phenyl-ethenesulfonyl)-1,2,3,4-tetrahydro-isoquinoline-7-carboxylic acid hydroxyamide |
| 113 | 2-Phenylmethanesulfonyl-1,2,3,4-tetrahydro-isoquinoline-7-carboxylic acid hydroxyamide |
| 114 | 2-(4-Nitro-benzenesulfonyl)-1,2,3,4-tetrahydro-isoquinoline-7-carboxylic acid hydroxyamide |
| 115 | 2-(3,4-Dimethoxy-benzenesulfonyl)-1,2,3,4-tetrahydro-isoquinoline-7-carboxylic acid hydroxyamide |
| 116 | 2-(4-Methoxy-benzenesulfonyl)-1,2,3,4-tetrahydro-isoquinoline-7-carboxylic acid hydroxyamide |
| 117 | 2-(Quinoline-8-sulfonyl)-1,2,3,4-tetrahydro-isoquinoline-7-carboxylic acid hydroxyamide |
| 118 | 2-(Thiophene-2-sulfonyl)-1,2,3,4-tetrahydro-isoquinoline-7-carboxylic acid hydroxyamide |
| 119 | 2-(3,5-Dichloro-benzenesulfonyl)-1,2,3,4-tetrahydro-isoquinoline-7-carboxylic acid hydroxyamide |
| 120 | 2-(3,4-Difluoro-benzenesulfonyl)-1,2,3,4-tetrahydro-isoquinoline-7-carboxylic acid hydroxyamide |
| 121 | 2-(4-Trifluoromethyl-benzenesulfonyl)-1,2,3,4-tetrahydro-isoquinoline-7-carboxylic acid hydroxyamide |
| 122 | 2-(5-Dimethylamino-naphthalene-1-sulfonyl)-1,2,3,4-tetrahydro-isoquinoline-7-carboxylic acid hydroxy amide |
| 123 | 2-(4-Bromo-benzenesulfonyl)-1,2,3,4-tetrahydro-isoquinoline-7-carboxylic acid hydroxyamide |
| 124 | 2-[4-(4-Dimethylamino-phenylazo)-benzenesulfonyl]-1,2,3,4-tetrahydro-isoquinoline-7-carboxylic acid hydroxyamide |
| 125 | 2-(2-Acetylamino-4-methyl-thiazole-5-sulfonyl)-1,2,3,4-tetrahydro-isoquinoline-7-carboxylic acid hydroxyamide |

*Compounds 68-105 (Example 7); compounds 106-125 (Example 8)

In another embodiment, the Formula I compounds may be prepared as a hydroxamic acid HDAC inhibitor library that can be utilized in screening methods known in the art. A process for the synthesis of library members is shown in Scheme 3, by way of example.

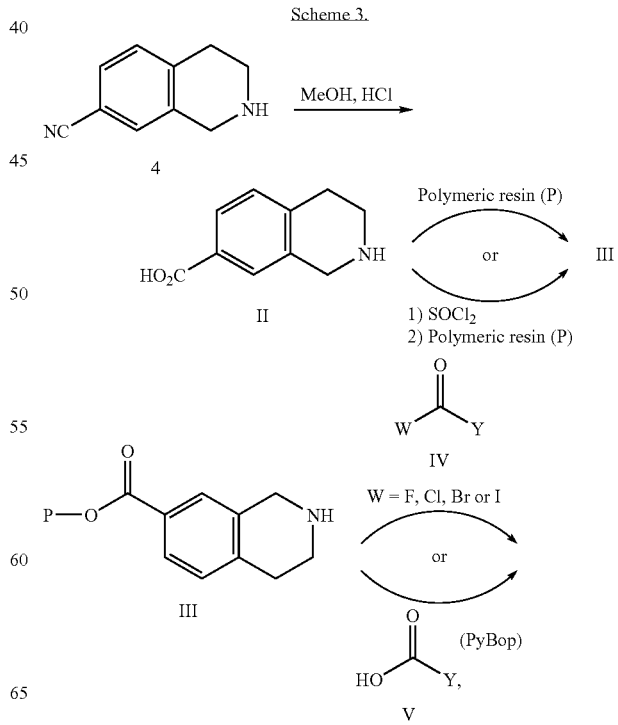

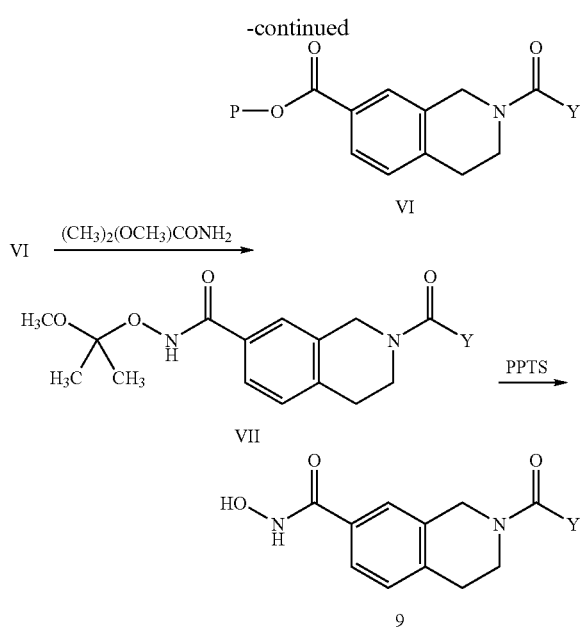

6-Cyanotetrahydroquinoline 4 is converted to 6-carboxytetrahydroquinoline II following any suitable method described in the art. See for example, Grunewald et al., *J. Med. Chem.* 1999, 42, 118-134, the contents of which is incorporated herein by reference in its entirety. 6-Carboxytetrahydroquinoline II is reacted with a polymeric resin (P) to give resin-immobilized tetrahydroquinoline III. Alternatively, 6-Carboxytetrahydroquinoline II is converted to the corresponding acid chloride followed by reaction with the polymeric resin (P) to give resin-immobilized tetrahydroquinoline III. Resin-immobilized tetrahydroquinoline III is reacted with an acyl halide IV. Alternatively, resin-immobilized tetrahydroquinoline III is reacted with a carboxylic acid V in the presence of a coupling reagent such as benzotriazol-1-yl-oxytripyrrolidinophosphonium hexafluorophosphate (PyBop), N,N'-carbonyldiimidazole, 1-cyclohexyl-3-3 (2-morpholinomethyl)-carbodiimide, N-(3-Dimethylaminopropyl)-N'-ethylcarbodiimide (EDC), and dicyclohexylcarbodiimide (DCC), to form N-acetyltetrahydroquinoline VI. N-acetyltetrahydroquinoline VI is reacted with $(CH_3)_2(OCH_3)ONH_2$, to form a (1-methoxy-1-methyl-ethoxy)-amide VII. (1-methoxy-1-methyl-ethoxy)-amide VII is reacted with a deprotecting compound such as pyridinium para-toluenesulfonate (PPTS) (See for example, Sternson et al., *Org. Lett.*, 2001, 26, 4239-4242, the contents of which is incorporated herein by reference in its entirety) to form hydroxamic acid compound 9, a Formula I compound.

The HDAC inhibition activity of the hydroxamic acid compounds of the present invention is assessed by standard assaying methods used in the art, such as for example, the one described by Carmen, et. al. *J. Biol. Chem.* 1996, 271, 15837-15844, the contents of which is incorporated herein by reference in its entirety. The inhibition of HDAC is assayed using [$^3$H]-labeled acetylated histones prepared in Jurkat_T cells which is used as the enzyme substrate. The hydroxamic acid HDAC inhibitor compounds of the present invention, dissolved in an appropriate solvent such as dimethylsulfoxide (DMSO), are pre-incubated with recombinant HDAC1 enzyme for about 30 minutes at about 4° C. in buffer containing about 40 mM Tris-Cl, pH of about 7.6, about 20 mM EDTA and about 50% glycerol. At about 37° C., the [$^3$H]-labeled acetylated histones are added and incubated for about 10 minutes. The released [$^3$H]-acetic acid is then extracted and quantified by scintillation count.

The assay described above is intended to exemplify one of several methods available for assessing the biological activity of hydroxamic acid HDAC inhibitor compounds of the invention to one skilled in the art, and is not intended, in any way, to limit the scope of the applicability of such assays to the compounds of the invention.

The hydroxamic acid HDAC inhibitor compound of the invention may be administered by any of the suitable routes to a mammal that are medically acceptable. The HDAC inhibitor compound is preferably administered orally (e.g., dietary) in capsules, suspensions or tablets. Methods for encapsulating compositions (such as in a coating of hard gelatin or cyclodextran) are known in the art (Baker, et al., "Controlled Release of Biological Active Agents", John Wiley and Sons, 1986). The hydroxamic acid HDAC inhibitor compounds can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers should be biocompatible, i.e., non-toxic, non-inflammatory, non-immunogenic and devoid of other undesired reactions at the administration site. Examples of pharmaceutically acceptable carriers include, for example, saline, commercially available inert gels, or liquids supplemented with albumin, methyl cellulose or a collagen matrix. Standard pharmaceutical formulation techniques can be employed, such as those described in "Remington: The Science and practice of Pharmacy", 20$^{th}$ ed. (2000), Lippincott, Williams & Wilkins, Philadelphia, Pa.

A "mammal" as described herein refers to both human and animal species in need of administration of an HDAC inhibitor.

As referred to herein, mammals "in need of administration" with HDAC inhibiting compounds, are those affected with symptoms or conditions that are treatable with HDAC inhibitors in a mammal as shown to be beneficial therapeutically or prophylactically. A beneficial outcome resulting from such treatment, may include, but is not limited to either a decrease in the severity of symptoms or delay in the onset of symptoms, or a substantial reversal of the symptom or condition.

The suitability of a given HDAC inhibitor compound for treatment of neurodegenerative disease can be assessed in any of a number of animal models for neurodegenerative disease. For example, mice transgenic for an expanded polyglutamine repeat mutant of ataxin-1 develop ataxia typical of spinocerebellar ataxia type 1 (SCA-1) are known (Burright et al., 1995, Cell 82: 937-948; Lorenzetti et al., 2000, Hum. Mol. Genet. 9: 779-785; Watase, 2002, Neuron 34: 905-919), and can be used to determine the efficacy of a given compound in the treatment or prevention of neurodegenerative disease. Additional animal models, for example, for Huntington's disease (see, e.g., Mangiarini et al., 1996, Cell 87: 493-506, Lin et al., 2001, Hum. Mol. Genet. 10: 137-144), Alzheimer's disease (Hsiao, 1998, Exp. Gerontol. 33: 883-889; Hsiao et al., 1996, Science 274: 99-102), Parkinson's disease (Kim et al., 2002, Nature 418: 50-56), amyotrophic lateral sclerosis (Zhu et al., 2002, Nature 417: 74-78), Pick's disease (Lee & Trojanowski, 2001, Neurology 56 (Suppl. 4): S26-S30, and spongiform encephalopathies (He et al., 2003, Science 299: 710-712) are known and can also be used to evaluate the efficacy of HDAC inhibitors in a similar manner.

Animal models are not limited to mammalian models. For example, *Drosophila* strains provide accepted models for a number of neurodegenerative disorders (reviewed in Fortini & Bonini, 2000, Trends Genet. 16: 161-167; Zoghbi & Botas, 2002, Trends Genet. 18: 463-471). These models include not only mutants bearing mutated fly genes, but also mutants bearing human transgenes with targeted mutations. Among the *Drosophila* models available are, for example, Spinocerebellar ataxias (e.g., SCA-1 (see, e.g., WO 02/058626), SCA-3 (Warrick et al., 1998, Cell 93: 939-949)), Huntington's disease (Kazemi-Esfarjani & Benzer, 2000, Science 287: 1837-1840), Parkinson's disease (Feany et al., 2000, Nature 404: 394-398; Auluck et al., 2002, Science 295: 809-810), age-dependent neurodegeneration (Palladino et al., 2002, Genetics 161: 1197-1208), Alzheimer's disease (Selkoe et al., 1998, Trends Cell Biol. 8: 447-453; Ye et al., 1999, J. Cell Biol. 146: 1351-1364), amyotrophic lateral sclerosis (Parkes et al., 1998, Nature Genet. 19: 171-174) and adrenoleukodystrophy.

Animals administered the compounds are evaluated for symptoms relative to animals not administered the compounds. A change in the severity of symptoms (e.g., a 10% or greater improvement in one or more symptoms), or a delay in the onset of symptoms, in treated versus untreated animals is indicative of therapeutic efficacy.

Dosage and Administration

An "effective amount" as referred to herein, relates to the amount of HDAC inhibitor compound (dose) that is capable of rendering a beneficial clinical outcome of the condition being treated with the HDAC inhibitor compound of the invention compared with the absence of such treatment. The effective amount of HDAC inhibitor compound administered will depend on the degree, severity, and type of the disease or condition, the amount of therapy desired, and the release characteristics of the pharmaceutical formulation. It will also depend on the subject's health, size, weight, age, sex and tolerance to specific compounds, which are determinable pharmaceutical parameters to those skilled in the field. Generally, treatment is considered "effective" if one or more symptoms of the disease or disorder improves (e.g., at least 10% relative to pre-treatment) during the course of treatment. The compounds of the invention can also be given to prevent or delay the onset of symptoms in an individual predisposed to such disorder, e.g., one predisposed to Huntington's chorea. A delay or absence of the onset of symptoms relative to the time one would expect such symptoms to arise in a similar individual not treated with the drug would indicate efficacy.

The present invention provides for pharmaceutical compositions comprising a therapeutically effective amount of an HDAC inhibitor as disclosed herein, in combination with a pharmaceutically acceptable carrier or excipient. The HDAC inhibitors employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds useful according to the invention may also be presented as liposome formulations.

In general a suitable dose will be in the range of 0.01 to 100 mg per kilogram body weight of the recipient per day, preferably in the range of 0.2 to 10 mg per kilogram body weight per day. The desired dose is preferably presented once daily, but may be dosed as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

In addition to their administration singly, the compounds useful according to the invention can be administered in combination with other known inhibitors of HDAC activity. In any event, the administering physician can adjust the amount and timing of drug administration on the basis of observations of one or more symptoms (e.g., motor or cognitive function as measured by standard clinical scales or assessments) of the disorder being treated.

The invention is illustrated by the following examples which are not intended to be limiting in any way.

EXAMPLES

Example 1

7-Nitro-1,2,3,4-tetrahydroisoquinoline hydrochloride (2)

1,2,3,4-tetrahydroisoquinoline (Aldrich T1,300-5, 100 gm) (11.6 g, 84.8 mmol) is added dropwise with care to stirred ice-cold concentrated $H_2SO_4$ (42.0 mL). Potassium nitrate (9.40 g., 93 mmol) is then added in small portions, taking care that the temperature of the reaction mixture does not rise above 5° C. After stirring overnight at room temperature the dark brown reaction mixture is added carefully to a stirred ice-cold concentrated NH$_4$OH solution. The basic red reaction mixture is extracted with chloroform (three times), and the combined chloroform extracts is washed with brine and dried over anhydrous Na$_2$SO$_4$. Evaporation of the solvent gives a dark brown oil (14.6 g) which was taken up in EtOH (65 mL) and cooled in an ice bath. Treatment of this reddish solution with concentrated HCl (11 mL) yields a viscous yellow precipitate of the hydrochloride salt which is filtered and crystallized from methanol (250 mL) to yield the product compound (2) as a solid (5.36 g, ~30% yield). Alternatively, flash chromatography may be used to purify the crude reaction mixture before crystallization.

Example 2

7-Amino-1,2,3,4-tetrahydroisoquinoline dihydrochloride (3)

7-Nitro-1,2,3,4-tetrahydroisoquinoline hydrochloride (2) from Example 1, is placed in a Parr shaker bottle (15.0 g, 69.9 mmol) dissolved in 95% EtOH (100 mL), and to the Parr shaker bottle is added concentrated HCl (10 mL), water (25 mL), and PtO$_2$ (0.5 g). The mixture is hydrogenated at 50 psi until no further drop in pressure was observed (about 4 hours). The yellowish suspension is filtered through Celite and evaporated to dryness to afford a yellowish solid which is made basic with 10% NaOH solution (adequate care is exercised in catalyst disposal). Extraction of the basic solution with CHCl$_3$ (three times), followed by drying over anhydrous Na$_2$SO$_4$ and evaporation of the solvent, yields a reddish yellow solid (9.54 g, 92.2%): mp=110-112. 7-Amino-1,2,3,4-tetrahydroisoquinoline dihydrochloride (3) is recrystallized from aqueous MeOH as buff colored needles, mp=290° C.

Example 3

7-Cyano-1,2,3,4-tetrahydroisoquinoline Hydrochloride (4)

7-Amino-1,2,3,4-tetrahydroisoquinoline dihydrochloride (3) from Example 2 (0.75 g, 5.1 mmol) is dissolved in concentrated HCl (1.75 mL) and water (2 mL) and stirred in an ice bath, giving a red solution. To this solution is added dropwise NaNO$_2$ (0.35 g, 5.1 mmol) dissolved in water (2 mL). After 15 minutes stirring, a positive starch-iodide test is obtained and the excess HNO$_2$ is destroyed by the addition of urea (0.10 g).

In a second flask, a solution of NaOH (0.50 g in 1.5 mL water) and KCN (1.63 g in 5 mL of water) is prepared, and benzene (5 mL) is added. The suspension is chilled in an ice bath, and to it is added a solution of Ni$_2$SO$_4$-6H$_2$O (1.3 g, 5 mmol) in 2.5 mL water). The color of the resulting mixture changes to yellow-brown. To this mixture is added dropwise with vigorous stirring the diazotized solution. Brisk evolution of N$_2$ is observed, and the reaction mixture is allowed to warm to room temperature over a period of 2 hours. The mixture is warmed to 50° C. in an oil bath for 1 hour, cooled to room temperature, made basic with 1 N NaOH, and filtered through Celite. The Celite bed is washed with methylene chloride, the filtrate is extracted with methylene chloride (three times), and the combined organic layers are washed with brine. Removal of the solvent after drying with Na$_2$SO$_4$ gives a dark black oil (0.60 g) which is distilled bulb to bulb (100-105° C., 0.15 mm Hg using a Kugelrohr or similar apparatus) to afford a colorless oil (0.30 g) which solidifies on cooling. The compound may be further purified by flash chromatography or prep HPLC. The resulting 7-Cyano-1,2,3,4-tetrahydroisoquinoline hydrochloride (4) is a colorless solid, m.p.=92-94° C.

Example 4

7-Methoxycarbonyl-1,2,3,4-tetrahydroiosquinoline hydrochloride (5)

7-Cyano-1,2,3,4-tetrahydroisoquinoline Hydrochloride (4) from Example 3 (0.205 g, 1.29 mmol) is added to a saturated methanolic HCl solution (20 mL, prepared by bubbling HCl in dry MeOH), and to the resulting suspension is added water (0.03 mL). The mixture is heated to reflux for 18 hours. The solution is cooled, and the solvent removed on a rotary evaporator to yield a colorless solid which is treated with 5% NaHCO$_3$. The solution was extracted with methylene chloride, dried over anhydrous Na$_2$SO$_4$, and evaporated to give a colorless semisolid (0.243 g, 98%). Recrystallization from methylene chloride-hexane produces white needles of 7-Methoxycarbonyl-1,2,3,4-tetrahydroiosquinoline hydrochloride (5), m.p.=216-218° C.

Example 5

7-Methoxycarbonyl-1-[arylcarbonyl or alkylcarbonyl)-1,2,3,4-tetrahydroisoquinoline hydrochloride (6)

Experimental conditions are those of standard coupling of acids (see Table 1) to amines. Alternatively, in several cases acid chlorides may be used in place of carboxylic acids. Table 1 shows carboxylic acid compounds 10-47.

Example 6

7-Methoxycarbonyl-1-[arylsulfonyl or alkylsulfonyl)-1,2,3,4-tetrahydroisoquinoline hydrochloride (7)

Experimental conditions are those of standard conditions for reacting sulfonyl chlorides (see Table 2) with amines to give sulfonamides. Table 2 shows sulfonyl chloride compounds 48-67.

Example 7

7-N-hydroxyamide-1-[arylcarbonyl or alkylcarbonyl]-1,2,3,4-tetrahydroisoquinoline (8)

To a solution of compound (6) from Example 5, (2 mmol) in methanol (~10 mL) is added at room temperature a 5% sodium hydroxide solution (10 mL). The mixture is stirred at room temperature for 4 hours. The solvent is evaporated and the residue diluted with water. The mixture is washed with methylene chloride, acidified with 10% HCl, extracted with ethyl acetate, then dried over MgSO$_4$. The solvent is evaporated to give the carboxylic acid.

To a solution of the carboxylic acid (1 mmol) in DMF (10 mL) is added (1-(3-dimethylaminopropyl)-3-ethylcarbodiimide hydrochloride (248 mg, 1.3 mmol) and hydroxybenzotriazole hydrate (162 mg, 1.2 mmol). The mixture is stirred at room temperature for 2 hours. Hydroxylamine hydrochloride (348 mg, 5 mmol) is added followed by triethylamine (696 μL, 5 mmol). After the mixture is stirred at room-temperature overnight, the solvent is evaporated. Water is added, and the mixture is extracted with EtOAc. The organic layer is washed with saturated solution of NaHCO$_3$ and brine, dried over MgSO$_4$, and evaporated to dryness. The residue is purified by column chromatography on silica gel with CH$_2$Cl$_2$/MeOH to give 7-N-hydroxyamide-1-[arylcarbonyl or alkylcarbonyl]-1,2,3,4-tetrahydroisoquinoline (8). Products 68-105 are shown in FIG. 3.

Example 8

7-N-hydroxyamide-1-[arylsulfonyl or alkylsulfonyl]-1,2,3,4-tetrahydroisoquinoline (9)

To a solution of compound (7) from Example 6, (2 mmol) in methanol (~10 mL) is added at room temperature a 5% sodium hydroxide solution (10 mL). The mixture is stirred at room temperature for 4 hours. The solvent was evaporated and the residue diluted with water. The mixture is washed with methylene chloride, acidified with 10% HCl, extracted with ethyl acetate, then dried over $MgSO_4$. The solvent is evaporated to give the carboxylic acid.

To a solution of the carboxylic acid (1 mmol) in DMF (10 mL) is added (1-(3-dimethylaminopropyl)-3-ethylcarbodiimide hydrochloride (248 mg, 1.3 mmol) and hydroxybenzotriazole hydrate (162 mg, 1.2 mmol). The mixture is stirred at room temperature for 2 hours. Hydroxylamine hydrochloride (348 mg, 5 mmol) is added followed by triethylamine (696 µL, 5 mmol). After the mixture is stirred at room-temperature overnight, the solvent is evaporated. Water is added, and the mixture is extracted with EtOAc. The organic layer is washed with saturated solution of $NaHCO_3$ and brine, dried over $MgSO_4$, and evaporated to dryness. The residue is purified by column chromatography on silica gel with $CH_2Cl_2$/MeOH to give 7-N-hydroxyamide-1-[arylsulfonyl or alkylsulfonyl]-1,2,3,4-tetrahydroisoquinoline (9). Products 106-125 are shown in FIG. 3.

Example 9

Synthetic Approach for Combinatorial Library Hydroxamic Acid HDAC Inhibitors

A synthesis of a library of HDAC inhibitors based on the 7-carboxyl-isoquinoline scaffold is shown in Scheme 2 below. 6-Cyanotetrahydroquinoline 4 is obtained by methods disclosed in the art. See for example, Grunewald et al., *J. Med. Chem.* 1997, 40, 3997-4005, the contents of which is incorporated herein by reference in its entirety. 6-Cyanotetrahydroquinoline 4 is converted to 6-Carboxytetrahydroquinoline II following the method described in the art by Grunewald et al., *J. Med. Chem.* 1999, 42, 118-134, the contents of which is incorporated herein by reference in its entirety. Attachment of 6-Carboxytetrahydroquinoline II to a resin to give resin-imobilized tetrahydroquinoline III and subsequent acylation in a combinatorial fashion with a variety or acids or acid chlorides is standard chemistry with many experimental examples known in the art. Resin-bound esters of the type VI can be aminated and cleaved from resin with reagents such as amines and $(CH_3)_2(OCH_3)ONH_2$. (1-methoxy-1-methyl-ethoxy)-amide VII is converted to the corresponding hydroxamic acid 9, following the method described by Sternson et al., *Org. Lett.*, (2001) 26, 4239-4242.

Example 10

HDAC Inhibition Assay

Inhibition of HDAC is assayed using [$^3$H]-labeled acetylated histones prepared in Jurkat_T cells used as the enzyme substrate (See for example, Carmen, A. A., Rundlett, S. E., Grunstein, M. *J. Biol. Chem.* (1996) 271, 15837-15844, the contents of which is incorporated herein by reference in its entirety). In this procedure the hydroxamic acid compounds of the present invention, in an appropriate solvent such as dimethylsulfoxide DMSO, are pre-incubated with recombinant HDACl enzyme for 30 minutes at 4° C. in buffer containing 40 mM Tris-Cl, pH=7.6, 20 mM EDTA and 50% glycerol. At 37° C., the [$^3$H]-labeled acetylated histones are added and incubated for about 10 minutes. The released [$^3$H]-acetic acid is then extracted and quantified by scintillation count.

All patents, patent applications, and published references cited herein are hereby incorporated by reference in their entirety. While this invention has been particularly illustrated and described with references to particular examples of preferred embodiments thereof, it will be understood by those skilled in the art that various changes in form and details may be made therein without departing from the scope and spirit of the invention encompassed by the appended claims.

What is claimed is:

1. A hydroxamic acid compound represented by formula (I):

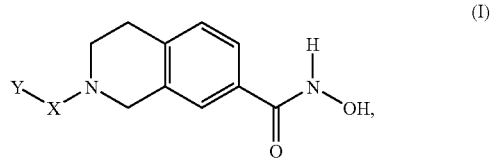

wherein:

X is selected from the group consisting of a carbonyl group (C=O), or a sulfonyl group ($SO_2$);

Y is selected from the group consisting of $C_1$-$C_6$ alkyl, $R_1(R_2)N$—$(CH_2)_n$—,

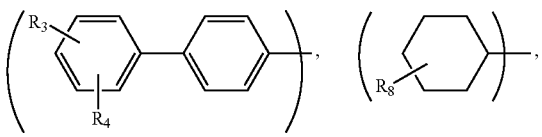

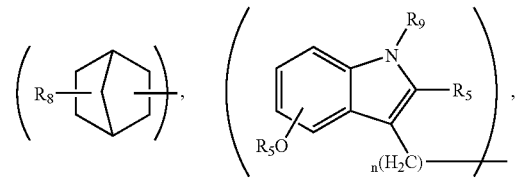

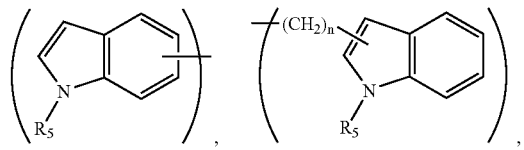

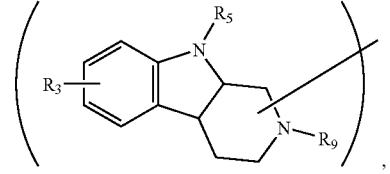

-continued

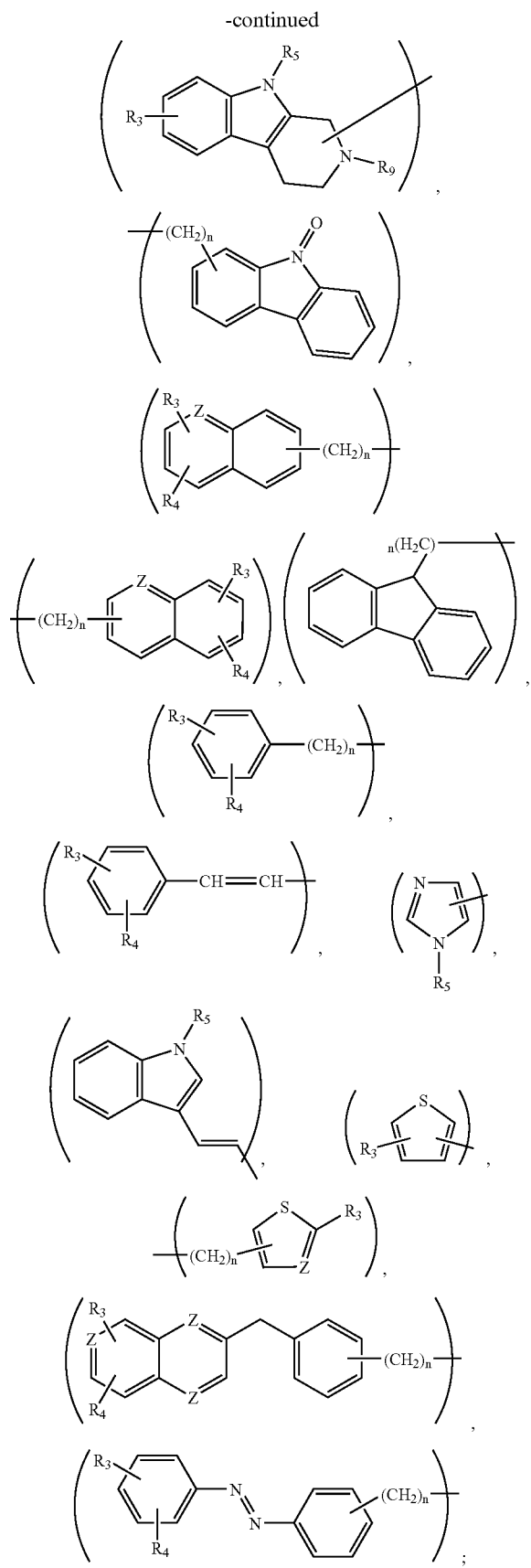

wherein:
R₁ and R₂ are each independently selected from the group consisting of hydrogen, straight chain lower alkyl, and branched lower alkyl;
R₁ and R₂, taken together with the nitrogen to which they are attached, form a heterocyclic ring, wherein said heterocyclic ring is optionally substituted with a substituted or unsubstituted lower alkyl group, or a substituted or unsubstituted benzyl group;
R₃ and R₄ are each independently selected from the group consisting of hydrogen, halogen, straight chain $C_1$-$C_8$ alkyl, $(R_1)(R_2)N$—$(CH_2)_n$—, $NH_2$—$C(=NH)$—$NH$—, $OR_5$, $CF_3$, $NO_2$, $R_7$—$C(=O)N(R_6)$—, imidazolyl, and pyrrolyl, wherein R₁ and R₂ are as defined above;
R₅ is hydrogen, $C_1$-$C_8$ alkyl, or benzyl;
R₆ is hydrogen, lower alkyl, or benzyl;
R₇ is $C_1$-$C_8$ alkyl, benzylalkyl, heteroalkyl or heteroaralkyl;
R₈ is hydrogen, —$(CH_2)_nN(R_1)(R_2)$, or $OR_5$, wherein R₁, R₂ and R₅ are as defined above;
R₉ is hydrogen, $C_1$-$C_8$ alkyl, or benzyl;
Z is —$C(R_3)$— or nitrogen (N), wherein R3 is as defined above; and
n is 0 to 6;
or hydrates, polymorphs, or pharmaceutically acceptable salts thereof.

2. The hydroxamic acid compound of claim 1, represented by formula (I):

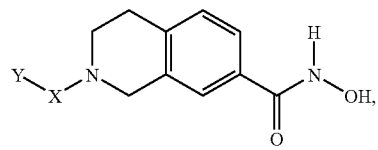

wherein:
X is a carbonyl group (C=O);
Y is selected from the group consisting of $R_1(R_2)N$—$(CH_2)_n$—,

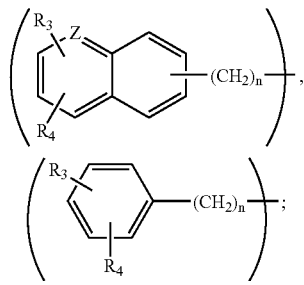

wherein:
R₁ and R₂ are each independently selected from the group consisting of hydrogen, straight chain lower alkyl, and branched lower alkyl;
R₁ and R₂, taken together with the nitrogen to which they are attached, form a heterocyclic ring, wherein said heterocyclic ring is optionally substituted with a substituted or unsubstituted lower alkyl group, or a substituted or unsubstituted benzyl group;
R₃ and R₄ are each independently selected from the group consisting of hydrogen, halogen, straight chain $C_1$-$C_8$ alkyl, $(R_1)(R_2)N-(CH_2)_n-$, $NH_2-C(=NH)-NH-$, $OR_5$, $CF_3$, $NO_2$, $R_7-C(=O)N(R_6)-$, imidazolyl, and pyrrolyl wherein $R_1$ and $R_2$ are as defined above;

$R_5$ is hydrogen, $C_1$-$C_8$ alkyl, or benzyl;

$R_6$ is hydrogen, lower alkyl, or benzyl;

$R_7$ is $C_1$-$C_8$ alkyl, benzylalkyl, heteroalkyl or heteroaralkyl;

Z is $-C(R_3)-$ or nitrogen (N), wherein R3 is as defined above; and n is 0 to 6;

or hydrates, polymorphs, or pharmaceutically acceptable salts thereof.

3. The hydroxamic acid compound of claim 1, wherein the hydroxamic acid compound is 2-(4-guanidino-benzoyl)-1,2,3,4-tetrahydro-isoquinoline-7-carboxylic acid hydroxyamide.

4. The hydroxamic acid compound of claim 1, wherein the hydroxamic acid compound is 2-(4-dimethylamino-benzoyl)-1,2,3,4-tetrahydro-isoquinoline-7-carboxylic acid hydroxyamide.

5. The hydroxamic acid compound of claim 1, wherein the hydroxamic acid compound is 2-(quinoline-8-carbonyl)-1,2,3,4-tetrahydro-isoquinoline-7-carboxylic acid hydroxyamide.

6. The hydroxamic acid compound of claim 1, wherein the hydroxamic acid compound is 2-((4-dimethylamino-phenyl)-acetyl)-1,2,3,4-tetrahydro-isoquinoline-7-carboxylic acid hydroxyamide.

7. The hydroxamic acid compound of claim 1, wherein the hydroxamic acid compound is 2-(4-dimethylamino-butyryl)-1,2,3,4-tetrahydro-isoquinoline-7-carboxylic acid hydroxyamide.

8. The hydroxamic acid compound of claim 1, wherein the hydroxamic acid compound is 2-(4-imidazol-1-yl-benzoyl)-1,2,3,4-tetrahydro-isoquinoline-7-carboxylic acid hydroxyamide.

9. The compound of claim 1 or claim 2 wherein R3 is halogen.

10. The compound of claim 1 or claim 2 wherein R4 is C1-C8 alkyl.

11. The compound of claim 1 or claim 2 wherein n=0.

12. The compound of claim 1 wherein R1 and R2 are independently selected from the group consisting of hydrogen, straight chain lower alkyl and branched lower alkyl.

13. The compound of claim 1 wherein R1 and R2, taken together with the nitrogen to which they are attached, form an unsubstituted heterocyclic ring.

14. The compound of claim 2 wherein Y is:

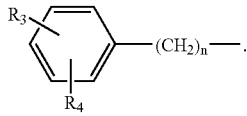

15. The compound of claim 2 wherein Y is:

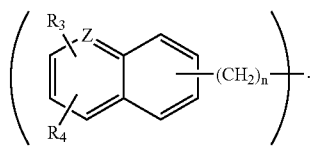

16. A pharmaceutical composition comprising a therapeutically effective amount of a hydroxamic acid compound of claim 1 in admixture with a pharmaceutically acceptable carrier for oral or parenteral administration.

17. The pharmaceutical composition of claim 16, wherein the hydroxamic acid compound is selected from the group consisting of:

2-(4-guanidino-benzoyl)-1,2,3,4-tetrahydro-isoquinoline-7-carboxylic acid hydroxyamide;

2-(4-dimethylamino-benzoyl)-1,2,3,4-tetrahydro-isoquinoline-7-carboxylic acid hydroxyamide;

2-(quinoline-8-carbonyl)-1,2,3,4-tetrahydro-isoquinoline-7-carboxylic acid hydroxyamide;

2-((4-dimethylamino-phenyl)-acetyl)-1,2,3,4-tetrahydro-isoquinoline-7-carboxylic acid hydroxyamide;

2-(4-dimethylamino-butyryl)-1,2,3,4-tetrahydro-isoquinoline-7-carboxylic acid hydroxyamide; and 2-(4-imidazol-1-yl-benzoyl)-1,2,3,4-tetrahydro-isoquinoline-7-carboxylic acid hydroxyamide.

18. A pharmaceutical composition comprising a therapeutically effective amount of a hydroxamic acid compound of claim 2 in admixture with a pharmaceutically acceptable carrier for oral or parenteral administration.

19. A method for treating a neurodegenerative disease that is a polyglutamine repeat disorder comprising administering the pharmaceutical composition of claim 16.

20. The method of claim 19 wherein the polyglutamine repeat disorder is Huntington's disease.

21. A process of preparing an hydroxamic acid compound represented by formula (I):

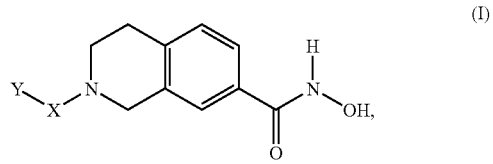

wherein:

X is a carbonyl group (C=O);

Y is selected from the group consisting of $C_1$-$C_6$ alkyl, $R_1(R_2)N-(CH_2)_n-$,

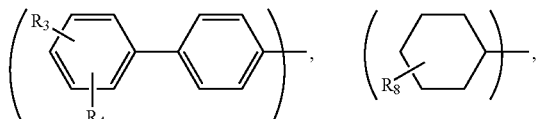

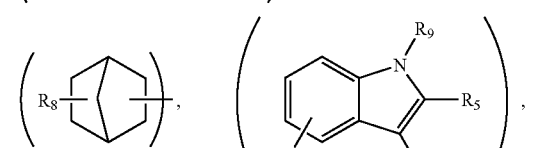

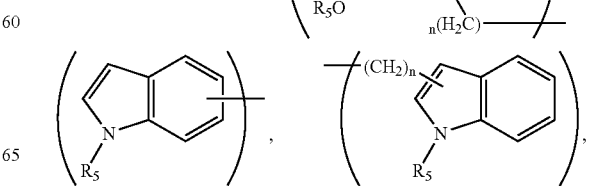

-continued

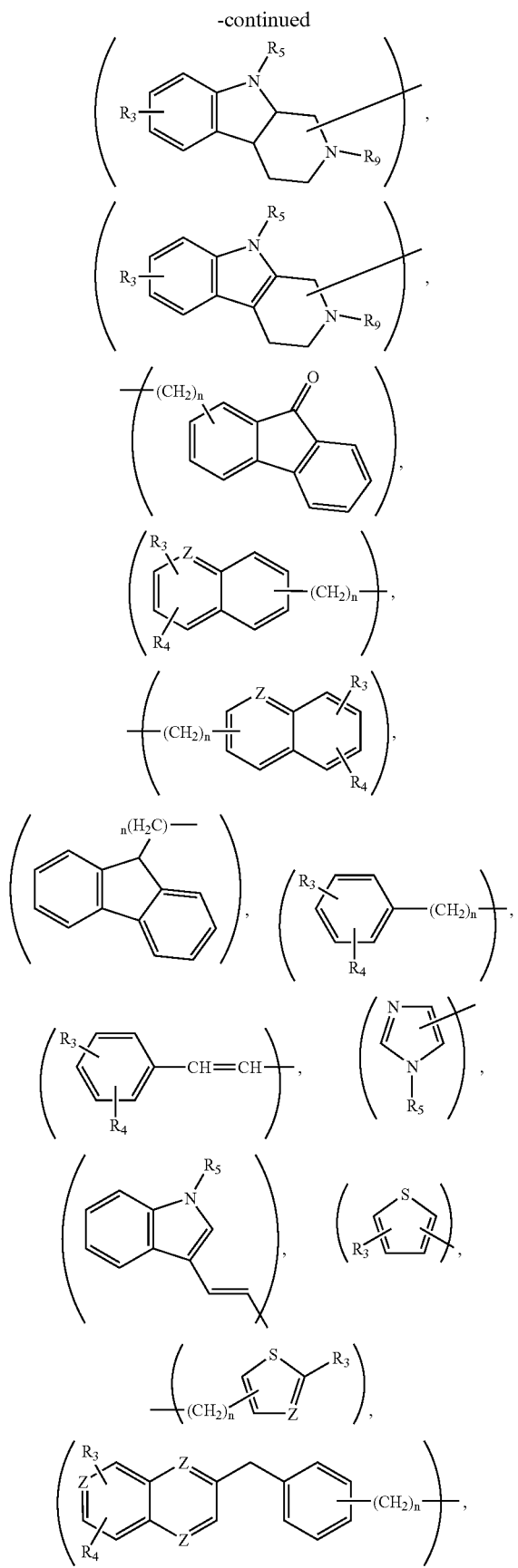

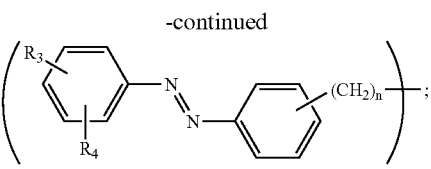

wherein:

R₁ and R₂ are each independently selected from the group consisting of hydrogen, straight chain lower alkyl, and branched lower alkyl;

R₁ and R₂, taken together with the nitrogen to which they are attached, form a heterocyclic ring, wherein said heterocyclic ring is optionally substituted with a substituted or unsubstituted lower alkyl group, or a substituted or unsubstituted benzyl group;

R₃ and R₄ are each independently selected from the group consisting of hydrogen, halogen, straight chain $C_1$-$C_8$ alkyl, $(R_1)(R_2)N$—$(CH_2)_n$—, $NH_2$—$C(=NH)$—$NH$—, $OR_5$, $CF_3$, $NO_2$, $R_7$—$C(=O)N(R_6)$—, imidazolyl, and pyrrolyl wherein R₁ and R₂ are as defined above;

R₅ is hydrogen, $C_1$-$C_8$ alkyl, or benzyl;

R₆ is hydrogen, lower alkyl, or benzyl;

R₇ is $C_1$-$C_8$ alkyl, benzylalkyl, heteroalkyl or heteroaralkyl;

R₈ is hydrogen, —$(CH_2)_nN(R_1)(R_2)$, or $OR_5$, wherein R₁, R₂ and R₅ are as defined above;

R₉ is hydrogen, $C_1$-$C_8$ alkyl, or benzyl;

Z is —$C(R_3)$— or nitrogen (N), wherein R3 is as defined above; and n is 0 to 6;

or hydrates, polymorphs, or pharmaceutically acceptable salts thereof, comprising the steps of;

reacting 1,2,3,4-tetrahydro-isoquinoline-7-carboxylic acid (Formula (II))

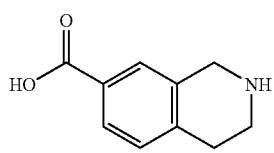

(II)

with a polymeric resin to form a compound of formula (III):

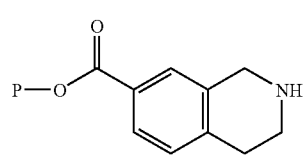

(III)

wherein P is a polymeric resin;

reacting the compound of formula (III) with an acylating compound of formula (IV):

(IV)

wherein W is a halogen, Cl, Br, or I, or with a compound of formula (V):

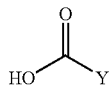

(V)

in the presence of a coupling reagent, to form a compound of formula (VI):

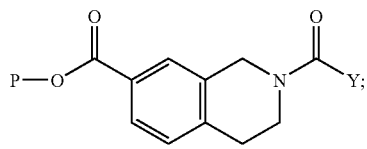

(VI)

reacting the compound of formula (VI) with $(CH_3)_2(OCH_3)ONH_2$, to form a compound of formula (VII):

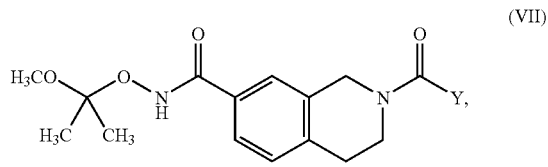

(VII)

reacting the compound of formula (VII) with pyridinium para-toluenesulfonate (PPTS) to give the compound of Formula (I).

22. The process of claim 21, wherein said polymeric resin is crosslinked.

23. The process of claim 21, wherein P is a polystyrene resin.

24. The process of claim 21, wherein said coupling reagent is selected from the group consisting of benzotriazol-1-yl-oxytripyrrolidinophosphonium hexafluorophosphate (Py-Bop), N,N'-carbonyldiimidazole, 1-cyclohexyl-3-3(2-morpholinomethyl)-carbodiimide, N-(3-Dimethylaminopropyl)-N'-ethylcarbodiimide (EDC), and dicyclohexylcarbodiimide (DCC).

25. The process of claim 21, wherein said coupling reagent is benzotriazol-1-yl-oxytripyrrolidinophosphonium hexafluorophosphate (PyBop).

26. The process for preparing a hydroxamic acid compound of claim 21, wherein said hydroxamic acid compound is represented by formula (I):

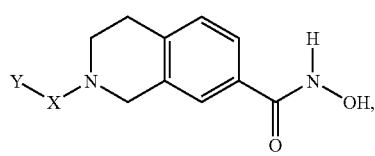

wherein:
X is a carbonyl group (C=O);
Y is selected from the group consisting of $R_1(R_2)N$—$(CH_2)_n$—,

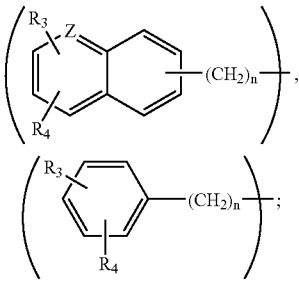

wherein:
$R_1$ and $R_2$ are each independently selected from the group consisting of hydrogen, straight chain lower alkyl, and branched lower alkyl;
$R_1$ and $R_2$, taken together with the nitrogen to which they are attached, form a heterocyclic ring, wherein said heterocyclic ring is optionally substituted with a substituted or unsubstituted lower alkyl group, or a substituted or unsubstituted benzyl group;
$R_3$ and $R_4$ are each independently selected from the group consisting of hydrogen, halogen, straight chain $C_1$-$C_8$ alkyl, $(R_1)(R_2)N$—$(CH_2)_n$—, $NH_2$—$C(=NH)$—$NH$—, $OR_5$, $CF_3$, $NO_2$, $R_7$—$C(=O)N(R_6)$—, imidazolyl, and pyrrolyl, wherein $R_1$ and $R_2$ are as defined above;
$R_5$ is hydrogen, $C_1$-$C_8$ alkyl, or benzyl;
$R_6$ is hydrogen, lower alkyl, or benzyl;
$R_7$ is $C_1$-$C_8$ alkyl, benzylalkyl, heteroalkyl or heteroaralkyl;
Z is —$C(R_3)$— or nitrogen (N), wherein R3 is as defined above; and
n is 0 to 6;
or hydrates, polymorphs, or pharmaceutically acceptable salts thereof.

27. The process of claim 21, wherein the hydroxamic acid compound is 2-(4-guanidino-benzoyl)-1,2,3,4-tetrahydro-isoquinoline-7-carboxylic acid hydroxyamide.

28. The process of claim 21, wherein the hydroxamic acid compound is 2-(4-dimethylamino-benzoyl)-1,2,3,4-tetrahydro-isoquinoline-7-carboxylic acid hydroxyamide.

29. The process of claim 21, wherein the hydroxamic acid compound is 2-(quinoline-8-carbonyl)-1,2,3,4-tetrahydro-isoquinoline-7-carboxylic acid hydroxyamide.

30. The process of claim 21, wherein the hydroxamic acid compound is 2-((4-dimethylamino-phenyl)-acetyl)-1,2,3,4-tetrahydro-isoquinoline-7-carboxylic acid hydroxyamide.

31. The process of claim 21, wherein the hydroxamic acid compound is 2-(4-dimethylamino-butyryl)-1,2,3,4-tetrahydro-isoquinoline-7-carboxylic acid hydroxyamide.

32. The process of claim 21, wherein the hydroxamic acid compound is 2-(4-imidazol-1-yl-benzoyl)-1,2,3,4-tetrahydro-isoquinoline-7-carboxylic acid hydroxyamide.

* * * * *